United States Patent [19]

Autant et al.

[11] Patent Number: 4,876,097

[45] Date of Patent: Oct. 24, 1989

[54] COMPOSITIONS FOR COATING FEEDING STUFF ADDITIVES INTENDED FOR RUMINANTS AND FEEDING STUFF ADDITIVES THUS COATED

[75] Inventors: Pierre Autant; Andre Cartillier, both of Commentry; Raymond Pigeon, Francheville, all of France

[73] Assignee: Rhone-Poulenc Sante, Courbevoie, France

[21] Appl. No.: 93,137

[22] Filed: Sep. 2, 1987

Related U.S. Application Data

[63] Continuation of Ser. No. 810,778, Dec. 19, 1985, abandoned.

[30] Foreign Application Priority Data

Dec. 20, 1984 [FR] France .................................. 84-19520
Dec. 20, 1984 [FR] France .................................. 84-19521

[51] Int. Cl.$^4$ .............................................. A23K 1/00
[52] U.S. Cl. .......................................... 426/74; 426/89; 426/656; 426/807; 424/438
[58] Field of Search ...................... 426/69, 89, 92, 623, 426/807, 74, 656; 424/35, 81

[56] References Cited

U.S. PATENT DOCUMENTS

| | | | |
|---|---|---|---|
| 3,562,806 | 2/1971 | Grant et al. | 426/69 |
| 3,829,564 | 8/1974 | Merry et al. | 426/92 |
| 4,177,255 | 12/1979 | Dannelly | 424/35 |
| 4,234,565 | 11/1980 | Flodin et al. | 424/81 |
| 4,256,785 | 3/1981 | Dannelly | 426/89 |

OTHER PUBLICATIONS

Wu et al, "Controlled Release Feed Additives for Ruminants", Controlled Release Pestic. Pharm. (1980), pp. 319–331.

*Primary Examiner*—R. B. Penland
*Attorney, Agent, or Firm*—Stevens, Davis, Miller & Mosher

[57] ABSTRACT

A composition for coating a biologically active substance which is stable in a medium in which the pH is greater than or equal to 5 and which permits the release of the active substance in a medium in which the pH is less than or equal to 3.5, comprises a film-forming, water-insoluble binder which possesses controlled hydrophilicity and is optionally slightly sensitive to pH variations, and a substance which is sensitive to pH variations (e.g. an inorganic filler, simple aminated substance, basic polymer or copolymer, chitosan). Pellets for feeding to ruminants consist of a core containing the biologically active substance, e.g. methionine or lysine, coated with this substance.

11 Claims, No Drawings

COMPOSITIONS FOR COATING FEEDING STUFF ADDITIVES INTENDED FOR RUMINANTS AND FEEDING STUFF ADDITIVES THUS COATED

This application is a continuation of application Ser. No. 810,728, filed Dec. 19, 1985 and now abandoned.

The present invention relates to compositions for coating feedingstuff additives intended for ruminants, which are stable in a medium in which the pH is equal to or greater than 5.5 and which permit the release of the feedingstuff additive in a medium in which the pH is less than or equal to 3.5.

When certain biologically active substances (drugs, enriched feedingstuffs) are administered to ruminants, enzymatic destruction of these substances takes place during passage through the rumen, this destruction being promoted by the residence time (a few hours to several days) and the pH (between 5 and 6).

It is consequently essential to be able to protect these biologically active substances by coatings which are stable at a pH greater than or equal to 5, i.e. which are stable in the first stomach of ruminants, which resist degradation by microorganisms, and which permit the release of the biologically active substances in a portion of the digestive system, more especially in the abomasum, in which the pH is less than or equal to 3.5. Whereas the protection period in the first stomach has to be relatively long (several hours to a few days), the release of the active substance in the abomasum must take place in a relatively short time (from a few minutes to 1 or 2 hours). To obtain such results, it is advantageous to be able to provide coatings for the active substances, the structure and composition of the coatings being such that they are insoluble in the rumen at a pH of between 5 and 6, but soluble, dispersed or greatly swollen in the abomasum at a pH less than 3.5, so as to release the active substance.

To produce such coatings, it has been proposed to use, inter alia, copolymers of maleic anhydride with another monomer, the copolymers being modified by the action of a primary-tertiary diamine on the anhydride groups, thereby forming aminated imide groups which provide the desired solubility (French Patent 1,536,774). Aminated cellulose derivatives are also know; they are obtained from an unsaturated cellulose derivative (ether, ester) which is reacted with a nitrogenous compound containing a mobile hydrogen atom, such as piperidine, morpholine or a secondary amine (French Patent No. 69/30,5622,081,320).

Furthermore, in British Patent No. 1,137,214, Australian Patent No. 454,117 and Belgian Patent No. 865,654, and South African Patent Application No. 70/04,813 as well as in French Patent No. 74/33,108-02,246,572 and U.S. Pat. No. 3,341,505, there are described copolymers of:

(a) a neutral ethylenic monomer such as methyl acrylate or methacrylate, styrene, acrylonitrile, vinyl acetate, and (b) an ethylenic monomer bearing a basic nitrogenous group such as diethylaminoethyl acrylate or methacrylate, tert-butylaminoethyl acrylate or methacrylate, morpholinoethyl methacrylate or vinylpyridines.

To coat feedingstuffs intended for feeding ruminants, it has been proposed to use styrene/vinylpyridine copolymers containing hydrophobic substances chosen from fatty acids containing 10 to 32 carbon atoms and polycarboxylic acids comprising 10 to 22 carbon atoms per carboxyl group, which improve the protection by decreasing the overall susceptibility of the coating film to attack by aqueous media of weakly acidic nature (French Patent Nos. 78/23,966-2,401,620). In such coating compositions, the hydrophobic substance reduces the wettability of the polymer, but has no effect on the release of the active principle in an acidic medium.

In French Patent Nos. 81/18,954-2,514,261, a coating is described consisting of a copolymer which is sensitive to pH variations, chosen from copolymers of styrene and vinylpyridines, and a non-water-soluble polymer which is insensitive to pH variations, chosen from cellulose acetobutyrate, ethylcellulose and cellulose propionate, this latter promoting the release of the active substance at a pH of between 1 and 2.5, and making it possible to reduce the extractability of the active substance in aqueous medium.

In French Patent Nos. 78/23,968 (2,401,621) the use is described of a hydrophobic polymer in which there is dispersed a substance which is soluble in an acidic medium (alkali metal phosphates, crosslinked basic polymers). However, it is not established that, to be effective, the binder has to possess controlled hydrophilicity which, where appropriate, according to the nature of the sensitive filler, has to depend on the pH.

It has now been found, and this forms the subject of the present invention, that active substances can be effectively coated for the purpose of administration to ruminants by means of a composition consisting essentially of a binding system which possesses controlled hydrophilicity, and which is optionally slightly sensitive to pH variations, combined with one or more substances which are very sensitive to pH variations and may be compatible or incompatible with the binding system.

The present invention therefore provides a composition suitable for coating a biologically active substance, which is stable at a pH greater than or equal to 5 and which permits the release of the biologically active substance at a pH less than or equal to 3.5, which composition comprises a film-forming, water-insoluble binding agent which possesses controlled hydrophilicity and which may be slightly sensitive to pH variations, and one or more substances which are very sensitive to pH variations chosen from inorganic fillers, simple aminated substances, basic polymers and copolymers and polyglucosamines.

In the context of the present invention, it is understood that the difference in sensitivity to pH must lie within a range between pH 1 and pH 7. The sensitivity to pH can be characterized by a modification in the physical and/or chemical properties of the substances between pH values above or equal to 5 and below or equal to 3.5. The modification in question is variable, and depends on the substances. In the case of a polymer, the modification may comprise swelling, which can proceed to the point of complete solubility, or may involve the rate of diffusion of water or aqueous solutions. In the case of inorganic or organic solid substances, the modification may involve a change in solubility or in the rate of solubilization. In the case of liquid substances, it can involve a change in miscibility. A slight sensitivity to variations in the pH of the binding system means that the binding properties are affected by the medium when the pH becomes less than or equal to 3.5, without it being implied in any way that the modifications induced are directly responsible for the release of the coated active substance on a large scale.

To produce the coating compositions according to the invention, the binding system which possesses controlled hydrophilicity and is optionally slightly sensitive to pH variations within the range in question, results from the combination of:

a film-forming component which provides for cohesion of the composition as a whole, a component for controlling the hydrophilic/hydrophobic balance, and optionally, a component which is slightly pH-sensitive, each part of the binder being able to fulfil several functions simultaneously, i.e. a single substance may function as more than one component e.g. as a film-forming and slightly pH-sensitive component or as a hydrophobic and slightly pH-sensitive component.

The film-forming component is chosen from natural or synthetic polymers which are capable of forming a coherent, non-water-soluble film, such as polyethylene waxes, cellulose ethers or esters such as ethylcellulose, cellulose acetate, propionate or acetobutyrate, vinyl derivatives such as polyvinyl acetate, acrylic derivatives such as polymethyl methacrylate, polymers and copolymers of butadiene and isobutylene, polyesters, polyamides and also non-water-soluble proteins such as zein. Zein, which is isolated from maize gluten, has the special advantage of being both the film-forming component needed for the mechanical stability of the coating and a slightly pHsensitive component which is useful for initiating the process of controlled release of the coated active principle in an acidic medium, as a result of the fact that its isoelectric point is in the region of 6.2

The component for controlling the hydrophilicity is, according to the nature of the binding system used, either a hydrophobic product such as a fatty substance, a paraffin wax, a natural wax, a synthetic wax (polyethylene wax), or a hydrophobic polymer (polyvinyl acetate or non-water-soluble cellulose derivative), or a hydrophilic or water-soluble derivative such as a water-soluble polymer (a cellulose, acrylic or maleic polymer) or a polyol such as glycerol, ethylene glycol, propylene glycol or dipropylene glycol.

The component which is slightly pH-sensitive is chosen from non-water-soluble substances possessing basic functions, which provide the binding system with an affinity for acidic media but which do not cause either the dissolution or the loss of cohesion of the binder, such as 6-ethoxy-1,2-dihydro-2,2,4-trimethylquinoline (ethoxyquin), fatty amines such as tallow or coconut propyleneamines or polypropyleneamines, basic amino acid derivatives such as esters or N-acylated derivatives of lysine or arginine, hydrophobic derivatives of nicotinic acid or hydrophobic proteins possessing a sufficiently high isoelectric point such as zein.

In such a system, the proportion of film-forming polymer by weight is generally greater than 50%.

Of particular interest is a binding system consisting of zein which may be used by itself or in association with at least one water-insoluble film-forming agent which is a fat, a paraffin wax, a natural wax (Carnauba wax, beeswax), a synthetic wax (polyethylene wax) or a polymer such as polyethylene, polyisobutylene, polyvinyl acetate or a water-insoluble cellulose derivative.

It is especially advantageous to use a binding system comprising zein in association with a water-insoluble cellulose derivative such as ethylcellulose or cellulose acetobutyrate.

Substances which are very sensitive to pH variations can be of diverse origins. They are generally chosen from inorganic fillers, simple aminated molecules, basic polymers and co-polymers and polyglucosamines. Among inorganic fillers, most special mention may be made of inorganic salts, the solubility of which is very low in a neutral medium and high in an acidic medium, such as calcium carbonate, and inorganic polymers which are characterized by rates of depolymerization and solubilization in water which differ greatly according to the pH, such as the complex polyphosphates of sodium, potassium, calcium, magnesium and aluminium. Among simple aminated substances, there may be mentioned amines, fatty amines, amino acid derivatives or basic protein derivatives, and hydrophobic derivatives of nicotinic acid and ethoxyquin (6-ethoxy-1,2-dihydro-2,2,4-trimethylquinoline). Among basic polymers and copolymers, there may be mentioned polymers or copolymers containing at least one basic amino group and having a nitrogen content of between 2 and 14%, such as amino derivatives of cellulose, polymers and copolymers of amino derivatives of acrylic, methacrylic and crotonic acids and polymers or copolymers of styrene or acrylonitrile with isomers or derivatives of vinylpyridine such as 2-vinylpyridine or 4-vinylpyridine or 2-methyl-5-vinylpyridine and polymers and copolymers of N-alkylated acrylates and methacrylates. Among polyglucosamines, most special mention may be made of chitosan, which is obtained by deacetylation of chitin which occurs abundantly in the shells of crustaceans.

The substances which are very sensitive to pH variations are used either in solution or in the form of powder, the particle size of which varies according to the thickness of the coating film which it is desired to obtain.

In the coating composition according to the present invention, it is necessary to achieve a balance between the various constituents, such that:

in neutral or slightly acidic medium, the active principle is not released as a result of having limited the hydrophilicity, in acidic medium, the fillers which are very sensitive to pH variations are accessible after a slow diffusion of the medium, which has been made possible as a result of the controlled hydrohilicity of the binder and, where appropriate, has been promoted by the presence of the substance which is slightly sensitive to pH variations. The dissolution or swelling of the substance which is very sensitive to pH variations then provides for the degradation of the envelope through swelling, splitting or bursting, and the release of the active principle.

In the coating composition according to the present invention, the amount of binder generally represents from 40 to 95% by weight of the composition, and the amount of the substance which is very sensitive to pH variations represents 5 to 50% by volume of the composition.

Of particular interest are coating compositions containing zein, ethylcellulose and a basic polymer or copolymer in proportions such that the texture of the coating layer obtained shows a morphology in the microphase range, the content of basic polymer or copolymer being less than 10% by weight.

Equally of particular interest are coating compositions containing zein, ethylcellulose and chitosan.

According to the present invention, the coating compositions can contain, apart from the binder and the substance which is very sensitive to pH variations, adjuvants the function of which is to facilitate the implementation of the techniques of preparing these compositions, or to improve their physicochemical characteristics. It can be advantageous to add plasticisers (triacetin, propylene glycol), lubricants (magnesium stearate), anti-static agents (triglycerides having ethylene oxide-treated chains), anti-caking agents (silica, calcium carbonate), fungicides, emulsifiers (condensates of sorbitan esters with ethylene oxide, sucro-glycerides), compatibility-promoting agents (natural or semi-natural gums, e.g. polysaccharides such as alginates, gum tragacanth, pectins, carragheenates, xanthan gum), cellulose ethers (carboxymethyl-, methyl- or hydroxypropylcellulose) or fillers such as inorganic salts, or sugar, starch or proteins. These various adjuvants generally only represent a few percent by weight of the coating composition.

The compositions according to the invention can be obtained by dispersing or dissolving the substance which is very sensitive to pH variations, optionally in combination with an adjuvant, in a solution or dispersion of the binder in an organic solvent or in a mixture of suitable organic solvents which are chosen in accordance with the specific nature of the binder. In general, the coating composition is obtained after the solvent or solvents has or have been evaporated off.

In certain cases, where organic or inorganic substances which are sensitive to pH variations are employed in pulverulent form, it can be advantageous to perform a pre-coating with adjuvants described above, for the purpose of adapting the filler/binder interface, e.g. to improve the impermeability of the system in neutral medium or to reduce it in an acidic medium.

To improve the impermeability of the system in neutral medium, especially for very water-soluble active substances, it is advantageous to use lamellar fillers of small particle size, such as mica, talc or aluminum, optionally pretreated with a hydrophobic agent such as stearic acid.

The coating compositions according to the present invention are especially useful for protecting various therapeutic or nutrient substances such as drugs, vitamins or amino acids, intended to be administered orally to ruminants. These coated substances are generally mixed with the animals' feed. The therapeutic or nutrient substances can take solid or liquid form.

The coated substances are preferably pellets in the form of microcapsules consisting of a central core surrounded by a continuous skin of the coating composition. However, the active substances can also be dispersed in the coating composition. In general, the coating composition represents 5 to 60% by weight of the pellet or dispersion.

The present invention also relates to the biologically active substances coated or dispersed in a coating composition described above.

The pellets can be obtained by application of known techniques. Depending on the nature of the coating composition and more especially on that of the non-water-soluble binder, use is made either of techniques of extrusion or spraying of solutions or emulsions in a fluidized bed, or of techniques of encapsulation in a molten or semi-molten medium, or of techniques of coating in a liquid medium such as coacervation.

The present invention also relates to the encapsulation of a liquid core consisting, for example, of a concentrated solution of the active substance in water or in a suitable organic solvent.

The pellets obtained according to the present invention are stable on storage and handling, do not deteriorate when the feedingstuffs are prepared and are not destroyed when they are consumed by the animals and, in particular, by crushing or grinding during mastication.

The size of the pellets will depend on the use which is to be made of them, and will be determined, more especially, according to the animal for which they are intended.

It is possible to coat active substances to obtain pellets the size of which is between 0.1 and 5 mm.

Most especially useful are the pellets which contain as active substances methionine, lysine or vitamins (vitamin A), the role of which is very important in the feeding of animals, and more especially ruminants.

To demonstrate the sensitivity of the coating compositions according to the invention to pH variations, tests are used which enable the release of the active material to be measured as a function of time at different pH values and, in particular, at pH 6 and pH 2, or at pH 5 and pH 1.5.

One test consists in making a disc in a film of the coating composition, on the upper face of which disc is placed a known amount of active material, the other face being in contact with the surface of a magnetically stirred buffered aqueous solution. The amount of active substance released into the aqueous solution is determined withdrawing aliquots, the same specimen being treated first at pH 6 and then at pH 2.

Another test consists in placing a known amount of active substance between 2 identical discs of the coating composition. This assembly, which is made leakproof by clamping the edges, is immersed in a specified amount of a magnetically stirred buffered aqueous solution. The amount of active substance released is monitored from the aliquot withdrawn at pH 6 and then, successively, at pH 2.

The release of the active substance in the form of pellets or microcapsules is examined by stirring, under specified conditions, a known quantity of pellets or microcapsules in the buffered medium maintained at constant pH and at a temperature of 40° C. The rates of release from a specimen subjected to different pH values, in particular to pH 6 and pH 2, are compared.

The Examples which follow, which are given without any implied limitation, illustrate the coating compositions according to the present invention, as well as their use for the preparation of coated active materials.

COMPARATIVE EXAMPLE 1

Using the fluidized bed technique, methionine (200 g), granulated beforehand into the form of spherical particles assaying at 98% and having a diameter of between 0.5 and 0.6 mm, is coated with a solution consisting of:

| | |
|---|---|
| cellulose acetobutyrate | 45 g |
| 2-vinylpyridine/styrene (70:30) copolymer | 15 g |
| tetrahydrofuran | 600 cc |

By film-coating, a coated product (260 g) assaying at 70% of methionine is obtained.

Release tests are performed at 40° C. in aqueous medium at pH 2 and pH 6, with stirring, at various time intervals.

The results are given in Table 1.

EXAMPLE 2

The procedure is as in Example 1, but the following solution is sprayed:

| | |
|---|---|
| celluloseacetobutyrate | 22.5 g |
| dipropylene glycol (1,2-propanediol) | 22.5 g |
| 2-vinylpyridine/styrene (70:30) copolymer | 15 g |
| tetrahydrofuran | 600 cc |

Release tests are performed at 40° C. in aqueous medium at pH 2 and pH 6, with stirring, at various time intervals.

The results are collected in Table 1.

TABLE 1

| | RELEASE AT pH 6 | | | | | RELEASE AT pH 2 | | | | |
|---|---|---|---|---|---|---|---|---|---|---|
| EX- | % AFTER | | | | RATE OF RELEASE | % AFTER | | | | RATE OF RELEASE |
| AMPLES | 1 h | 2 h | 3 h | 5 h | g/s | 30 min | 1 h | 2 h | 5 h | g/s |
| 1 | 3 | 5 | 7 | 9 | $2.5 \times 10^{-5}$ | | 4 | 5 | 10 | $2.5 \times 10^{-5}$ |
| 2 | 5 | 9 | 13 | 21 | $6.4 \times 10^{-5}$ | 100 | | | | $>3 \times 10^{-3}$ |

These results show the favourable effect of adding a water-soluble hydrophilic adjuvant.

COMPARATIVE EXAMPLE 3

Using the fluidized bed technique, methionine (200 g), granulated beforehand into the form of spherical particles assaying at 98% and having a diameter of between 0.5 mm and 0.6 mm, is coated with a solution composed of:

| | |
|---|---|
| celluloseacetobutyrate | 30 g |
| dipropylene glycol | 30 g |
| micronised polyphosphates of aluminium, calcium and sodium, diameter less than 15 microns | 90 g |
| tetrahydrofuran | 600 cc |

By simple film-coating, a product (332 g), assaying at 57% of methionine is obtained in 2 hours.

Release tests are performed at 40° C. in acidic aqueous medium at pH 1.5 or 5, with stirring, at various time intervals.

The results are given in Tables 2 and 3.

COMPARATIVE EXAMPLE 4

The procedure is as in Example 3, but with micronised polyphosphates (90 g) replaced by N-tallow-propylenediamine (6.7 g).

The results are given in Tables 2 and 3.

EXAMPLE 5

The procedure is as in Example 3, but with N-tallow-propylenediamine (6.7 g) added in addition.

The results are given in Tables 2 and 3.

EXAMPLE 6

The procedure is as in Example 5, but with N-tallow-propylenediamine replaced by N-coconut-dipropylene-triamine (6.7 g).

The results are given in Tables 2 and 3.

EXAMPLE 7

The procedure is as in Example 5, but with N-tallow-propylenediamine replaced by N-coconut-poly-propylenediamine (molecular mass in the region of 390; 6.7 g).

The results are given in Tables 2 and 3.

TABLE 2

| EXAMPLE | METHIONINE TITRE % | RATE OF RELEASE AT pH 1.5 (g/s) | RATE OF RELEASE AT pH 5 (g/s) | RATIO OF RATES pH 1.5/pH 5 |
|---|---|---|---|---|
| 3 | 57 | $1.7 \times 10^{-3}$ | $5.1 \times 10^{-4}$ | 3 |
| 4 | 73 | $6.5 \times 10^{-5}$ | $3.7 \times 10^{-5}$ | 2 |
| 5 | 55 | $6.7 \times 10^{-4}$ | $3.6 \times 10^{-4}$ | 19 |
| 6 | 56 | $1.1 \times 10^{-3}$ | $4.6 \times 10^{-5}$ | 24 |
| 7 | 56 | $9.2 \times 10^{-4}$ | $1.9 \times 10^{-5}$ | 48 |

TABLE 3

| EX- | % OF METHIONINE RELEASED at pH 1.5 after | | | % OF METHIONINE RELEASED at pH 5 after | | | |
|---|---|---|---|---|---|---|---|
| AMPLES | 30 min | 1 h | 2 h | 1 h | 2 h | 4 h | 5 h |
| 3 | 90 | 100 | | 39 | 79 | | |
| 4 | 5 | 8 | 12 | 5 | 8 | 12 | 14 |
| 5 | 17 | 51 | 100 | 5 | 8 | 13 | 17 |
| 6 | 42 | 84 | 100 | 5 | 8 | | 18 |
| 7 | 31 | 72 | 100 | 7 | 8 | 12 | 13 |

EXAMPLE 8

To a mixture consisting of ethanol (10 cc) and dichloromethane (10 cc) there are added zein (5 g) and chitosan (0.5 g), the particle size of which is 40 to 63 microns and the $NH_2$ group content of which is 7%.

A film 200 microns thick is poured on a horizontal glass plate. After 1 hour's drying at 40° C. at reduced pressure (20 mm Hg; 2.7 kPa), an opaque film 50 microns thick is obtained. Two discs 30 mm in diameter are cutout and methionine (feed-grade; 100 mg) is placed between them. The assembly, which is made leakproof by clamping the edges, is immersed in a magnetically stirred buffered aqueous solution (150 cc). The amount of methionine released is monitored on withdrawn aliquots.

The amounts of methionine released at pH 6 and then successively at pH 2 are given in Table 4.

EXAMPLE 9

Under the same conditions as in Example 8, a film is prepared from zein (5 g), chitosan (0.5 g), the particle size of which is from 80 to 125 microns and the $NH_2$ group content of which is 7%, and calcium carbonate (aragonite) (0.5 g), the average particle size of which is 0.2 micron.

The results are given in Table 4.

EXAMPLE 10

Under the same conditions as in Example 8, a film is prepared from zein (5 g), ethylcellulose (0.5 g) and chitosan (0.5 g) used in Example 9.

The results are given in Table 4.

EXAMPLE 11

Under the same conditions as in Example 8, a film is prepared from zein (5 g), ethoxyquin (0.5 g) and chitosan (0.5 g) used in Example 9.

The results are given in Table 4.

TABLE 4

| EX-AMPLES | RELEASE AT pH 6 AFTER 24 HOURS mg METHIONINE | RELEASE AT pH 2 AFTER 2 H mg METHIONINE | RELEASE AT pH 2 AFTER 5 H mg METHIONINE |
|---|---|---|---|
| 8 | 20 | 40 | 95 |
| 9 | 24 | 46 | 91 |
| 10 | 13 | 27 | 73 |
| 11 | 31.5 | 42 | 88 |

EXAMPLE 12

Using the fluidized bed technique, methionine (350 g), granulated beforehand into the form of a spherical particles assaying at 98% and having a diameter of between 0.6 and 1 mm, is coated with a solution/dispersion having the following composition:

| | |
|---|---|
| Zein | 80 g |
| Polyvinyl acetate | 30 g |
| Ethylcellulose | 10 g |
| Chitosan (particle size: 40–80 microns; $NH_2$ group content: 7%) | 10 g |
| Triacetin | 10 g |
| 1,2-Dichloroethane | 500 cc |
| Ethanol | 500 cc |
| Anti-static (Labrasol, Gattefosse registered trademark) | 3 cc |

By simple film-coating, coated pellets assaying at 86% of methionine are obtained in 5 hours.

The release of methionine is determined by dispersing pellets (200 mg) in a buffered solution (200 cc) magnetically stirred at 300 rpm. The amount of methionine released is monitored on withdrawn aliquots, the test being carried out on different specimens at pH 6 and pH 2.

The results are collated in Table 5.

EXAMPLE 13

Coating of methionine is performed with a coating composition identical to that used in Example 10, but containing only 5 g of chitosan, the particle size of which is less than 80 microns and the $NH_2$ group content of which is 7%.

A tank equipped with a Wurster system is used.

After 3 hours, pellets assaying at 72.5% of methionine are obtained.

The results are collated in Table 5.

COMPARATIVE EXAMPLE 14

The procedure is as in Example 13, but using a coating formulation not containing a substance sensitive to pH variations and having the following composition:

| | |
|---|---|
| Zein | 120 g |
| Triacetin | 10 g |
| 1,2-Dichloroethane | 500 cc |
| Ethanol | 500 cc |
| Anti-static (Labrasol) | 3 cc |

Pellets assaying at 72.5% of metionine are obtained. The results are collated in Table 5.

TABLE 5

| EX-AMPLES | METHIONINE TITRE % | RELEASE AT pH 6 AFTER 24 HOURS % | RELEASE AT pH 2 AFTER 2 H % | RELEASE AT pH 2 AFTER 5 H % |
|---|---|---|---|---|
| 12 | 86 | 85 | 76 | 100 |
| 13 | 74.5 | 16 | 99 | |
| 14 | 72.5 | 100 | | |

COMPARATIVE EXAMPLE 15

Using the fluidized bed technique, methionine (200 g) granulated beforehand into the form of spherical particles assaying at 98% and having a diameter between 0.5 and 0.6 mm, is coated with a solution in tetrahydrofuran of a composition (60 g) consisting of ethycellulose (75%) and 2-vinylpyridine/styrene (70:30) copolymer (25%).

Tests on release of the methionine are performed at 40° C. in aqueous medium at pH 2 and pH 6, with stirring, at various time intervals.

The results are given in Table 6.

EXAMPLE 16

The procedure is as in Example 15, but using a coating composition consisting of ethylcellulose (45%), dipropylene glycol (30%) and 2-vinylpyridine/styrene (70:30) copolymer (25%).

The results are given in Table 6.

EXAMPLE 17

The procedure is as in Example 15, but using a coating composition consisting of ethylcellulose (37.5%), dipropylene glycol (37.5%) and 2-vinylpyridine/styrene (70:30) copolymer (25%).

The results are given in Table 6.

EXAMPLE 18

The procedure is as in Example 15, but using a coating composition consisting of ethylcellulose (40%), propylene glycol (40%) and 2-vinylpyridine/styrene (70:30) copolymer (20%).

The results are given in Table 6.

EXAMPLE 19

The procedure is as in Example 15, but using a coating composition consisting of ethylcellulose (45%), propylene glycol (30%) and 2-vinylpyridine/styrene (70:30) copolymer (25%).

The results are given in Table 6.

COMPARATIVE EXAMPLE 20

The procedure is as in Example 15, but using a coating composition consisting of ethylcellulose (75%) and 2-methyl-5-vinylpyridine/styrene (80:20) copolymer (25%).

The results are given in Table 6.

EXAMPLE 21

The procedure is as in Example 15, but using a coating composition consisting of ethylcellulose (41.25%), propylene glycol (33.75%) and 2-methyl-5-vinylpyridine/styrene (80:20) copolymer (25%).

The results are given in Table 6.

COMPARATIVE EXAMPLE 22

The procedure is as in Example 15, but using a coating composition consisting of ethylcellulose (80%) and 2-methyl-5-vinylpyridine/styrene (80:20) copolymer (20%).

The results are given in Table 6.

EXAMPLE 23

The procedure is as in Example 15, but using a coating composition consisting of ethylcellulose (40%), propylene glycol (40%) and 2-methyl-5-vinylpyridine/styrene (80:20) copolymer (20%).

The results are given in Table 6.

COMPARATIVE EXAMPLE 24

Using the fluidized bed technique, Lysine monohydrochloride (200 g), granulated beforehand in the form of spherical particles assaying at 85% and having a diameter of between 1 and 1.25 mm, is coated with a solution in tetrahydrofuran of a composition (200 g) consisting of ethylcellulose (75%) and 2-vinylpyridine/styrene (70:30) copolymer (25%).

Tests on release of the lysine monohydrochloride are performed at 40° C. in aqueous medium at pH 2 and pH 6, with stirring, at various time intervals.

The results are given in Table 7.

EXAMPLE 25

The procedure is as in Example 24, but using a coating composition consisting of ethylcellulose (37.5%), propylene glycol (37.5%) and 2-vinylpyridine/styrene (70:30) copolymer (25%).

The results are given in Table 7.

TABLE 7

| EX-AMPLES | % OF LYSINE MONOHYDROCHLORIDE RELEASED AT pH 2 | | | | | % OF LYSINE MONOHYDROCHLORIDE RELEASED AT pH 6 AFTER | | | | |
|---|---|---|---|---|---|---|---|---|---|---|
| | 30 min | 1 h | 2 h | 3 h | 5 h | 1 h | 2 h | 3 h | 5 h | 24 h |
| 24 | 2 | 2 | 2 | 2 | 7 | 2 | 2 | 2 | 5 | |
| 25 | 96 | 100 | | | | | | 1 | 6 | 65 |

EXAMPLE 26

Zein (10 g) is dissolved in a stirred mixture consisting of ethanol (20 cc) and dichloromethane (20 cc) at a temperature in the region of 20° C. In the solution obtained, calcium carbonate (calcite) (4 g), the average particle size of which is 1 to 2 microns, is dispersed with vigorous stirring.

A film of thickness 350 microns is poured on a horizontal glass plate. After evaporation of the solvent at a temperature in the region of 20° C., followed by drying at 40° C. under reduced pressure (20 mm Hg; 2.7 kPa) for 1 hour 40 minutes, an opaque film is obtained, the thickness of which is 54 microns.

Using a hollow punch, a disc 30 mm in diameter is cut from this film, and methionine (feed-grade; 100 mg) is placed on its upper face. The lower face of the disc is maintained in contact with a magnetically stirred buffered aqueous solution.

The amount of methionine released is monitored on withdrawn aliquots, the same specimen being tested first at pH 6 and then at pH 2 without intermediate drying. The results obtained are collated in Table 8.

EXAMPLE 27

The procedure is as in Example 26, but with calcium carbonate powder replaced by a complex polyphosphate (4 g) based on $Na_2O$, $CaO$, $P_2O_5$ and $Al_2O_3$, the average particle size of which is 5.7 microns and which is characterized by a ratio of rates of solubility at pH 2 and pH 6 of the order of 400.

The results obtained are collated in Table 8.

COMPARATIVE EXAMPLE 28

By way of comparison, a film consisting of zein alone is prepared under the conditions of Example 26.

The results obtained are collated in Table 8.

TABLE 6

| EX-AMPLES | % OF METHIONINE RELEASED AT pH 2 after: | | | | % OF METHIONINE RELEASED at pH 6 after: | | | | |
|---|---|---|---|---|---|---|---|---|---|
| | 30 min | 1 h | 2 h | 5 h | 1 h | 2 h | 3 h | 5 h | 24 h |
| 15 | | 3 | 5 | 9 | 2 | 3 | 4 | 5 | |
| 16 | 44 | 78 | 100 | | | 1 | | 2 | |
| 17 | 96 | 100 | | | | 2 | 3 | 6 | |
| 18 | 5 | 23 | 76 | 100 | 1 | 2 | 3 | 5 | 11 |
| 19 | 10 | 50 | 92 | 100 | 1 | 2 | 3 | 4 | |
| 20 | | 9 | | | | | | 3 | 15 |
| 21 | 98 | | | | | | | 5 | 10 |
| 22 | 2 | | | | | | | 3 | 5 |
| 23 | | 96 | | | | | | 9 | 17 |

TABLE 8

| EXAMPLES | RELEASE AT pH 6 AFTER 24 HOURS mg METHIONINE | RELEAEE AT pH 2 AFTER 5 H mg METHIONINE | AFTER 24 H mg METHIONINE |
| --- | --- | --- | --- |
| 26 | 1 | 2.5 | 41.6 |
| 27 | 2 | 6 | 34.4 |
| 28 | 2 | 3 | 13 |

COMPARATIVE EXAMPLE 29

Zein (5 g) is dissolved in a mixture consisting of ethanol (10 cc) and dichloromethane (10 cc) at a temperature in the region of 20° C.

A film of thickness 200 mcirons is poured on a horizontal glass plate. After 1 hours's drying at 40° C. under reduced pressure (20 mm Hg; 2.7 kPa), an opaque film 50 microns thick is obtained.

2 discs 30 mm in diameter are cut out, between which methionine (feed-grade; 100 mg) is placed. The assembly, which is made leakproof by clamping at the edges, is immersed in a magnetically stirred buffered aqueous solution (150 cc).

The amounts of methionine released at pH 6 and then, in succession, at pH 2 are given in Table 9.

EXAMPLE 30

Under the conditions of Example 26, a film is prepared from zein (5 g) and triacetin (0.5 g).

The results are given in Table 9.

EXAMPLE 31

Under the conditions of Example 26, a film is prepared from zein (5 g), triacetin (0.5 g) and polyvinyl acetate (0.5 g) the molecular weight of which is in the region of 12,000 and the softening point of which is between 60 and 70° C.

The results are given in Table 9.

EXAMPLE 32

Under the conditions of Example 26, a film is prepared from zein (5 g) and ethoxyquin (0.5 g).

The results are given in Table 9.

TABLE 9

| EXAMPLES | RELEASE AT pH 6 AFTER 24 HOURS mg METHIONINE | RELEASE AT pH 2 AFTER 2 H mg METHIONINE | AFTER 5 H mg METHIONINE |
| --- | --- | --- | --- |
| 29 | 19 | | 13 |
| 30 | 8 | | 11 |
| 31 | 15 | | 59.5 |
| 32 | 6 | | 19.7 |

COMPARATIVE EXAMPLE 33

According to the fluidized bed technique, with a tank equipped with a WURSTER system, methionine (350 g), granulated beforehand into the form of spherical particles assaying at 98% and having a mean diameter of between 0.5 and 0.63 mm, is coated with a solution/dispersion, the composition of which by weight is as follows:

| | |
| --- | --- |
| Zein | 90 g |
| Ethylcellulose (Hercules grade N 22) | 30 g |
| Triacetin | 10 g |
| 1,2-dichloroethane | 500 cc |
| Ethanol | 500 cc |
| Antistatic (Labrasol, Gattefosse registered trademark) | 3 cc |

After 3 hours, uniformly coated pellets assaying at 73.6% of methionine are obtained.

The release of methionine is determined by dispersing granules (8 g) thus prepared in a buffered solution (1 litre) at 40° C. which is stirred magnetically and maintained at constant pH.

The amount of methionine released is monitored on withdrawal aliquots; the tests are performed at pH 6 and pH 2.

The results are collated in Table 10.

EXAMPLE 34

The procedure is as in Example 33, but with the addition of sodium potassium aluminum polyphosphate (75-90 microns; 20 g).

The results are collated in Table 10.

COMPARATIVE EXAMPLE 35

The procedure is as in Example 33, but using a coating solution having the following composition:

| | |
| --- | --- |
| Ethylcellulose (Hercules grade N 22) | 90 g |
| Triacetin | 10 g |
| 1,2-Dichloroethane | 500 cc |
| Ethanol | 500 cc |
| Antistatic | 3 cc |

The results are collated in Table 10.

EXAMPLE 36

The procedure is as in Example 35, but with the addition of sodium potassium aluminum polyphosphate (75-90 microns; 20 g).

The results are collated in Table 10.

EXAMPLE 37

The procedure is as in Example 35, but using a coating solution/dispersion having the following composition:

| | |
| --- | --- |
| Zein | 90 g |
| Triacetin | 10 g |
| 1,2-Dichloroethane | 500 cc |
| Ethanol | 500 cc |

-continued

| | |
|---|---|
| Antistatic | 3 cc |

The results are collated in Table 10.

EXAMPLE 38

The procedure is as in Example 35, but with the addition to the coating composition of a styrene/2-vinylpyridine copolymer (29.5:69.5 by weight; 20 g) of specific viscosity 0.592 measured at a concentration of 5 g/liter in dimethylformamide at 20° C.

The results are collated in Table 10.

EXAMPLE 39

The procedure is as in Example 33, but with the addition to the coating composition of a styrene/2-vinylpyridine copolymer (20 g) identical to that used in Example 38.

The results are collated in Table 10.

COMPARATIVE EXAMPLE 40

The procedure is as in Example 33, but using a coating composition having the following composition:

| | |
|---|---|
| Zein | 80 g |
| Ethylcellulose | 20 g |
| Polyvinyl acetate | 10 g |
| Triacetin | 10 g |
| 1,2-Dichloroethane | 500 cc |
| Ethanol | 500 cc |
| Antistatic (Labrasol) | 3 cc |

The results are collated in Table 10.

EXAMPLE 41

The procedure is as in Example 40, but with the addition to the coating solution of styrene/2-vinylpyridine copolymer (20 g) identical to that used in Example 38.

The results are collated in Table 10.

| | |
|---|---|
| Zein | 60 g |
| Ethylcellulose (Hercules grade N 22) | 30 g |
| Triacetin | 10 g |
| 2-Vinylpyridine/styrene (70:30) copolymer | 30 g |
| 1,2-Dichloroethane | 500 cc |
| Ethanol | 500 cc |
| Antistatic (Labrasol, Gattefosse registered trademark) | 3 cc |

The specific viscosity of the 2-vinylpyridine/styrene copolymer is 0.560 measured at a concentration of 5 g/liter in dimethylformamide at 20° C.

After 3 hours, uniformly coated pellets assaying at 72.1% of methionine are obtained.

The release of the methionine is determined under the conditions described in Example 33.

The results are collated in Table 11.

EXAMPLE 43

The procedure is as in Example 42, but with the addition of only 10 g of 2-vinylpyridine/styrene (70:30) copolymer.

The results are collated in Table 11.

EXAMPLE 44

The procedure is as in Example 43, but using a 2-vinylpyridine/styrene (70:30) copolymer the specific viscosity of which is 0.610.

The results are collated in Table 11.

EXAMPLE 45

The procedure is as in Example 43, but with the 2-vinylpyridine/styrene (70:30) copolymer replaced by a 2-methyl-5-vinylpyridine/styrene (77.5:22.5) copolymer the specific viscosity of which is 0.496.

The results are collated in Table 11.

EXAMPLE 46

TABLE 10

| EXAMPLE | METHIONINE TITRE % | RELEASE AT pH 6 | | RELEASE AT pH 2 | |
|---|---|---|---|---|---|
| | | AFTER 6 H % | AFTER 24 H % | AFTER 2 H % | AFTER 5 H |
| 33 | 73.6 | 10.5 | 19 | 7.5 | 9.2 |
| 34 | 72.9 | 5.6 | 14.6 | 55 | 94 |
| 35 | 79.7 | 2.5 | 8 | 2.8 | 4.2 |
| 36 | 75.5 | 3 | 10 | 3 | 4 |
| 37 | 78 | 90 | 100 | 100 | |
| 38 | 82.7 | 32.5 | 75.5 | 50 | 91 |
| | | | | 67 in 8 min | |
| 39 | 72 | 10 | 2 | 92 in 30 min | |
| 40 | 74.3 | 13 | 17 | 8.4 | 22 |
| 41 | 73.5 | 23 | 25 | 97 in 15 min | |

COMPARATIVE EXAMPLE 42

According to the fluidized bed technique, with a tank equipped with a WURSTER system, methionine (350 g), granulated beforehand into the form of spherical particles assaying at 98% and having a mean diameter of between 0.5 and 0.63 mm, is coated with a solution/-dispersion, the composition of which by weight is as follows:

The procedure is as in Example 43, but with the 2-vinylpyridine/styrene (70:30) copolymer replaced by a 2-vinylpyridine homopolymer.

These results are collated in Table 11.

EXAMPLE 47

The procedure is as in Example 43, but with the 2-vinylpyridine/styrene (70:30) copolymer replaced by a 2-vinylpyridine/styrene (90:10) copolymer.

The results are collated in Table 11.

EXAMPLE 48

The procedure is as in Example 43, but with the 2-vinylpyridine/styrene (70:30) copolymer replaced by a crosslinked 2-vinylpyridine/2-hydroxyethyl methacrylate copolymer.

The results are collated in Table 11.

TABLE 11

| EX-AMPLE | METHIONINE TITRE % | RELEASE AT pH 6 | | RELEASE AT pH 2 AFTER | | | |
|---|---|---|---|---|---|---|---|
| | | AFTER 6 H % | AFTER 24 H % | 15 min % | 30 min % | 1 H % | 2 H % |
| 42 | 72.1 | 10 | 26 | 100 | | | |
| 43 | 72.0 | 10 | 18 | 63 | 100 | | |
| 44 | 74.9 | 2.0 | 6.8 | 35 | 85 | 100 | |
| 45 | 74.4 | 4.5 | 8.6 | 69 | 94 | 100 | |
| 46 | 74.0 | 2.3 | 4.5 | 3.8 | 5.0 | 8.1 | 12.6 |
| 47 | 75.2 | 3.3 | 6.7 | 14.9 | 26.5 | 40.3 | 77.4 |
| 48 | 74.6 | 2.2 | 3.7 | | | 3.6 | 13.7 |

COMPARATIVE EXAMPLE 49

According to the fluidized bed technique, with a tank equipped with a WURSTER system, lysine hydrochloride (350 g), granulated beforehand into the form of spherical particles assaying at 85% and having a mean diameter of between 0.63 and 0.8 mm, is coated with a solution/dispersion the composition of which is identical to that described in Example 42.

The release of the lysine hydrochloride is determined under the conditions described in Example 33.

The results are collated in Table 12.

EXAMPLE 50

The procedure is as in Example 49, but with an increase in the level of coating, the coating composition being the same.

The results are collated in Table 12.

EXAMPLE 51

The procedure is as in Example 49, but using a coating composition consisting of:

| | |
|---|---|
| Zein | 82 g |
| Ethylcellulose (Hercules grade N 22) | 41 g |
| Triacetin | 13.7 g |
| 2-Vinylpyridine/styrene (70:30) copolymer | 13.7 g |
| Aluminium (STAPA 4 nl paste containing 65% of aluminium) | 100 g |
| 1,2-Dichloroethane | 683 cc |
| Ethanol | 683 cc |
| Antistatic (Labrasol, Gattefosse registered trademark) | 3 cc |

The results are collated in Table 12.

EXAMPLE 52

The procedure is as in Example 51, but replacing 100 g of STAPA 4 nl paste by 230 g of the same paste so as to have 150 g of aluminum in the coating composition.

The results are collated in Table 12.

EXAMPLE 53

The procedure is as in Example 52, but with the 2-vinylpyridine/styrene (70:30) copolymer replaced by a 2-methyl-5-vinylpyridine/styrene (77.5:22.5) copolymer the specific viscosity of which is 0.496.

The results are collated in Table 12.

TABLE 12

| EX-AMPLE | LYSINE.HCl TITRE % | RELEASE AT pH 6 | | RELEASE AT pH 2 AFTER | | |
|---|---|---|---|---|---|---|
| | | AFTER 6 H % | AFTER 24 H % | 15 min % | 30 min % | 1 H % |
| 49 | 67.5 | 100 | | 100 | | |
| 50 | 51.2 | 13.2 | 75.5 | 37.4 | 100 | |
| 51 | 50.2 | 40.7 | 88.6 | 57.9 | 100 | |
| 52 | 47.5 | 4.7 | 60.2 | 34.6 | 80.3 | 100 |
| 53 | 46.8 | 5.8 | 61.1 | 32.4 | 81.2 | 100 |

We claim:

1. A composition suitable for coating a bilogically active substance, which is stable at a pH greater than or equal to 5 and which permits the release of the biologically active substance at a pH less than or equal to 3.5, which composition comprises:

40 to 95% by weight of a film-forming, waterinsoluble binding agent which possesses controlled hydrophilicity and which may be slightly sensitive to pH variations, the said binding agent being selected from the group consisting of a combination of a water-insoluble filmforming cellulose derivative and an agent for controlling the hydrophilic/hydrophobic balance selected from the group consisting of polyols in a weight ratio of cellulose derivative to polyol of from 1:1 to 1.5:1; zein; and a combination of zein and an agent for controlling the hydrophilic/hydrophobic balance selected from the group consisting of water-insoluble cellulose derivative in a weight ratio of 2:1 to 10:1;

and 60 to 5% by weight of a pH sensitive substance selected from the group consisting of a polymer or copolymer containing at least one basic amino group and having a nitrogen content between 2 and 14% selected from the group consisting of amino derivatives of cellulose, polymers of amino derivatives of acrylic and methacrylic acids, copolymers of styrene with a vinylpyridine, and chitosan.

2. Pellets in the form of microcapsules intended for oral administration to animals, comprising a core containing a biologically active substance protected by a coating composition according to claim 1.

3. Pellets according to claim 2, in which the coating composition represents between 5 and 60% by weight of the coated pellet.

4. Pellets according to claim 2, in which the biologically active substance is a drug, vitamin or amino acid.

5. Pellets according to claim 2, in which the biologically active substance is methionine or lysine.

6. A composition according to claim 1, which also contains a plasticizer for the said binding agent.

7. A composition according to claim 6, in which the binding agent comprises zein and includes triacetin as a plasticizer for said zein.

8. A composition according to claim 6, in which the said binding agent also comprises an additional hydrophobic film-forming polymer.

9. A composition according to claim 8, in which the said additional film-forming polymer is polyvinyl acetate.

10. A composition according to claim 1, in which the said polyol is glycerol, ethylene glycol, propylene glycol or dipropylene glycol.

11. A composition according to claim 1, which contains in addition a lamella filler selected from the group consisting of mica, talc and aluminum.

* * * * *